United States Patent
Seo

(10) Patent No.: US 11,885,840 B2
(45) Date of Patent: Jan. 30, 2024

(54) METHOD OF MEASURING TEMPERATURE CHANGE AND SAR OF ARTIFICIAL HIP JOINT IMPLANT USING MAGNETIC RESONANCE IMAGING EQUIPMENT

(71) Applicant: KOREA RESEARCH INSTITUTE OF STANDARDS AND SCIENCE, Daejeon (KR)

(72) Inventor: Youngseob Seo, Daejeon (KR)

(73) Assignee: KOREA RESEARCH INSTITUTE OF STANDARDS AND SCIENCE, Daejeon (KR)

( * ) Notice: Subject to any disclaimer, the term of this patent is extended or adjusted under 35 U.S.C. 154(b) by 160 days.

(21) Appl. No.: 17/708,707

(22) Filed: Mar. 30, 2022

(65) Prior Publication Data

US 2022/0326288 A1    Oct. 13, 2022

(30) Foreign Application Priority Data

Mar. 30, 2021    (KR) .................. 10-2021-0041323

(51) Int. Cl.
G01R 29/08    (2006.01)
A61F 2/46    (2006.01)
A61F 2/32    (2006.01)

(52) U.S. Cl.
CPC ............ G01R 29/0857 (2013.01); A61F 2/32 (2013.01); A61F 2/4657 (2013.01); *A61F 2002/4672* (2013.01)

(58) Field of Classification Search
CPC .. A61F 2/32; A61F 2/4657; A61F 2002/4672; G01R 29/0857; G01R 33/288; G01R 33/58
See application file for complete search history.

(56) References Cited

U.S. PATENT DOCUMENTS

| 2002/0040185 A1* | 4/2002 | Atalar | H01Q 1/362 |
| | | | 600/423 |
| 2007/0236229 A1* | 10/2007 | Onishi | G01R 29/0885 |
| | | | 324/632 |
| 2018/0064365 A1* | 3/2018 | Srinivasan | A61G 11/00 |

FOREIGN PATENT DOCUMENTS

KR    10-2019-0021958 A    3/2019

OTHER PUBLICATIONS

Korean Office Action for related KR Application No. 10-2021-0041323 dated May 26, 2021 from Korean Intellectual Property Office.
Peter Nordbeck et al., "Spatial Distribution of RF-Induced E-Fields and Implant Heating in MRI", Magnetic Resonance in Medicine, Jul. 29, 2008, pp. 312-319, No. 60.

(Continued)

*Primary Examiner* — Omer S Khan
(74) *Attorney, Agent, or Firm* — Paratus Law Group, PLLC

(57) ABSTRACT

A method of measuring a specific absorption rate (SAR) of a hip joint implant using magnetic resonance imaging (MRI), includes: arranging the hip joint implant in a human lower body-shaped phantom; arranging an electric field sensor around the hip joint implant; providing radio frequency (RF) energy according to an MRI sequence to the human phantom; and calculating the SAR of the hip joint implant from strength of an electric field measured by the electric field sensor.

6 Claims, 11 Drawing Sheets

(56) References Cited

OTHER PUBLICATIONS

Y Seo, "MO-FG-CAMPUS-IeP3-01: Evaluation of Specific Absorption Rate and Temperature Increase Induced by Artificial Medical Implants During MRI Scan", Medical Physics, Jun. 7, 2016, pp. 3725, vol. 43.
Sung-Min Park et al., "Calculation of MRI-Induced Heating of an Implanted Medical Lead Wire With an Electric Field Transfer Function", Journal of Magnetic Resonance Imaging, Oct. 29, 2007, pp. 1278-1285, vol. 26.
Youngseob Seo et al., "Measurement and evaluation of specific absorption rate and temperature elevation caused by an artificial hip joint during MRI scanning", Scientific Reports, Jan. 13, 2021, pp. 1-12.

\* cited by examiner

| | Acetabular cup (110) | | | Cup linear (120) | Femoral head (130) | Femoral stem (140) | | Combined model |
|---|---|---|---|---|---|---|---|---|
| | Plasmacup SC | | | Ceramic insert | Ceramic head | Excia 8/10 cementless | | |
| Modeling | | | | | | | | |
| Material | Titanium | Polyethylene | Ceramic | Ceramic | Chromium | Chromium | Titanium | |

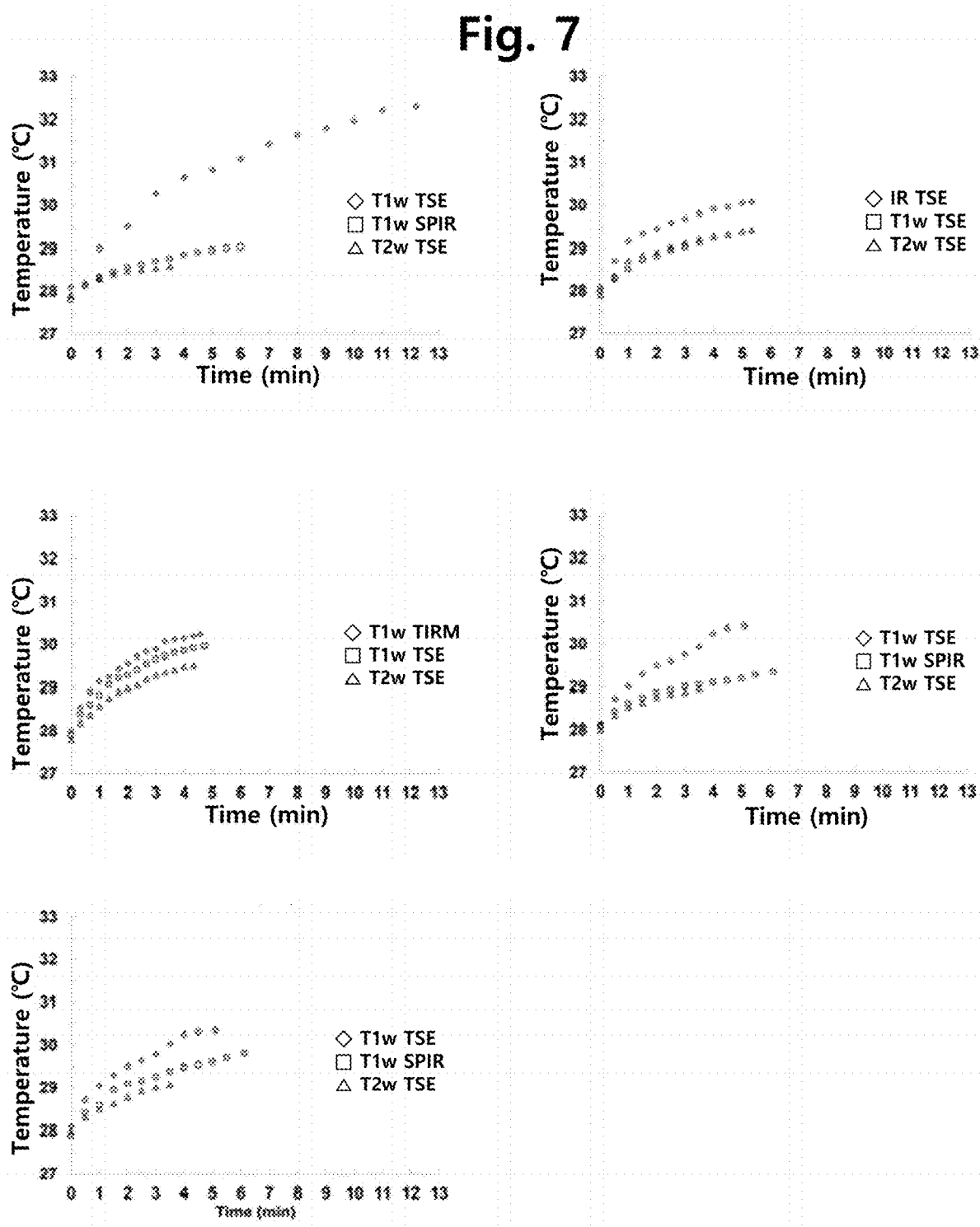

METHOD OF MEASURING TEMPERATURE CHANGE AND SAR OF ARTIFICIAL HIP JOINT IMPLANT USING MAGNETIC RESONANCE IMAGING EQUIPMENT

CROSS-REFERENCE TO RELATED APPLICATION

This application claims priority to Korean Patent Application No. 10-2021-0041323 (filed on Mar. 30, 2021), which is hereby incorporated by reference in its entirety.

BACKGROUND

The present invention relates to a method of measuring a temperature change and a specific absorption rate (SAR) of a hip joint implant using magnetic resonance imaging (MRI).

Magnetic resonance imaging (MRI) has an important role in medical diagnosis of diseases. High-field MRI has rapidly adopted in the magnetic resonance (MR) community for both clinical applications and researches over the past few decades. An increase in signal-to-noise ratio (SNR), decreased acquisition time and/or increased image resolution become important advantages of high-field MRI.

In MRI, it is important to accurately measure a specific absorption rate (SAR) of radio frequency (RF) energy absorbed by a human body. According to the International Electrotechnical Commission (IEC) standards, an average SAR value is limited to 4 W/kg for the body and 3.2 W/kg for the head for six minutes. In the standards of the United States Food and Drug Administration (US FDA), an average SAR value is limited to 3 W/kg when the head is scanned for ten minutes and 4 W/kg when the body is scanned for fifteen minutes. American Society for Testing and Materials (ASTM International) has established technical standards for evaluating RF heating of passive implantable medical devices during MRI scans.

Meanwhile, millions of joint replacements are performed every year worldwide and the number of joint replacements is increasing every year. In the past, entire hip joint replacement was significantly restricted to the elderly or individuals with limited movement associated with other comorbidities. In these days, however, patients require so-called high-performance artificial hip joint to meet their expectations and aspirations. Replacing a damaged hip joint with an artificial device has been a widely practiced operation in orthopedic surgery over the past few decades.

SUMMARY

As the clinical use of high-field magnetic resonance imaging (MRI) scanners increases, magnetic resonance (MR) safety becomes an important issue. A major safety concern during MRI scans is the heating of metallic medical implants that have absorbed high radio-frequency (RF) energy. The heating of the medical implants varies depending on the RF power, a static magnetic field strength, a shape and position of the implant, a pulse sequence, and/or imaging parameters.

Commercial MRI scanners provide specific absorption rate (SAR) levels estimated for each scan under average conditions without implants. The SAR levels are calculated using RF waveforms, sequence parameters, system calibration, coil factors, patient's weight and height, etc. However, the SAR values displayed by clinical MRI scanners are unreliable and much higher local SAR induced by the metal implants may damage tissues. A risk of hyperthermic tissue damage is relatively severe in patients with numb limbs and in patients under anesthesia during MRI scans.

In the related art, simulations using only a single pulse sequence were performed on the implanted metal material, and there was a large difference between a simulated temperature and a measured temperature at a tip of a titanium alloy implant. Local SAR levels in the head and tail parts of the implants are higher than those in the body part of the implants. The maximum temperature rise occurred at a tip of the implant and a minimum temperature rise occurred at a body part of the implant. In another related art, a maximum difference between a temperature in numerical analysis and a temperature in experiment was up to 81.3%.

The present invention is directed to providing a method of measuring a temperature change, which is capable of solving the above-described problems caused by the related art.

According to an aspect of the present invention, there is provided a method of measuring the SAR of a hip joint implant using MRI, including arranging the hip joint implant in a human phantom, arranging an electric field sensor around the hip joint implant, providing an RF energy to the human phantom according to an MRI sequence, and calculating the SAR of the hip joint implant from the strength of an electric field measured by the electric field sensors.

According to another aspect of the present invention, there is provided a method of measuring temperature rise of a hip joint implant using MRI, including arranging the hip joint implant in a human phantom, arranging a plurality of temperature sensors on the hip joint implant, providing an RF energy to the human phantom according to an MRI sequence, and measuring temperature changes of the hip joint implant by the temperature sensors, and calculating the SAR of the hip joint implant from the measured temperatures by the temperature sensors.

BRIEF DESCRIPTION OF THE DRAWINGS

The above and other objects, features and advantages of the present invention will become more apparent to those of ordinary skill in the art by describing exemplary embodiments thereof in detail with reference to the accompanying drawings, in which:

FIG. 7 shows experimentally measured temperatures as a function of scan time via fiber-optic Bragg grating temperature sensors at one tip location on the left side of artificial hip implants for three different MRI sequences at five different MRI scanners;

DETAILED DESCRIPTION

In an embodiment of the present invention, numerical simulations of radio frequency (RF) energy delivery are performed to predict specific absorption rate (SAR) levels in an anatomical model consisting of a homogeneous cylinder, sphere, or head. The SAR levels for various pulse sequences may vary in a wide range. In almost all cases, radiologists, physicists, and technicians do not have tools to independently check power levels, and thus it is desirable to directly estimate SAR values regardless of levels calculated by magnetic resonance imaging (MRI) scanners.

In the present embodiment, SAR levels of metallic hip joint implants are measured, and a risk of injury caused by RF induction heating of hip joint implants from different vendors is evaluated during high-field MRI scans. Experiments and computer simulations are performed by investigating spatial distributions of an electric field (E-field) that induces heat.

MRI Systems

MRI systems and sequences, which are used in the present embodiment, are as follows:

a T1w turbo spin echo (TSE) sequence, a T2w TSE and a T1w spectral pre-saturation with inversion recovery (SPIR) of an Achieva 1.5T system (in Philips Healthcare); a T1w TSE, a T2w TSE and an inversion recovery (IR) TSE sequence of a Signa EXCITE 1.5T system (in GE Healthcare); a T1w TSE, a T2w TSE and a T1 turbo inversion recovery magnitude (TIRM) sequence of a MAGNETOM Verio 3.0T system (in Siemens Healthcare); and a T1w TSE, a T2w TSE and a T1w SPIR sequence of two identical Achieva 3.0T system (in Philips Healthcare).

SAR values were measured in the systems and sequences described above. Three different MRI sequences having various SAR values provided by the MRI systems were used in scanners.

RF excitation power was transmitted by an integrated RF body coil (multi-transmission mode="NO" in 3.0 T Philips). In the present embodiment, a 4-channel or 8-channel body array coil is used as a receiving coil. An experiment was performed on a phantom that mimics a human body without conducting an experiment on a human or sampling on human tissue.

A whole body SAR is a value obtained by dividing total power absorbed by the whole body by a weight of the whole body. An "effective weight" of the phantom is a weight of the whole body absorbing the same amount of RF power as a 21 L of gelled saline phantom. An effective weight of 21 kg (=33% of the equivalent Korean adult body weight) was input to an MRI system when the MRI system is registered.

Shape of Phantom

Figure 1:
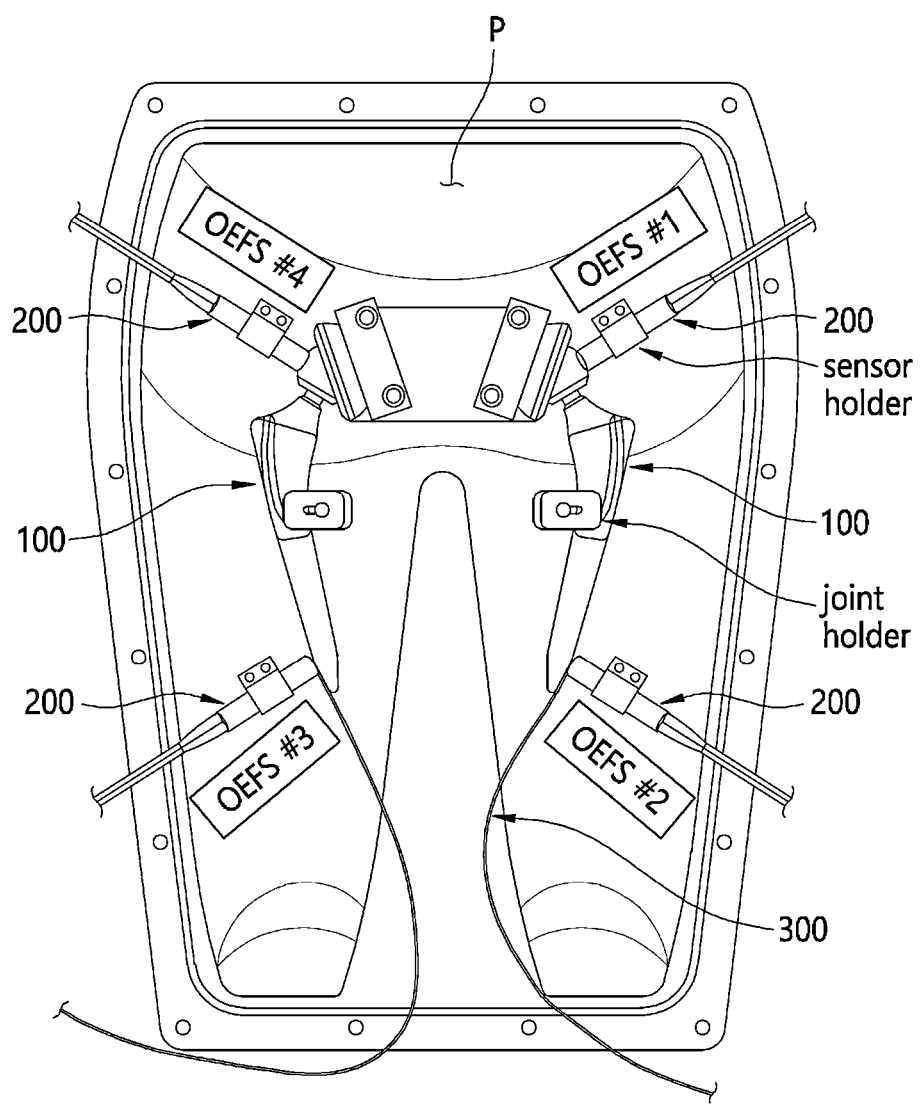
FIG. 1 shows locations of four optical electric field sensors and two fiber-optic Bragg grating temperature sensors which are arranged on the surface of an artificial hip joint in the phantom.
Figure 2:
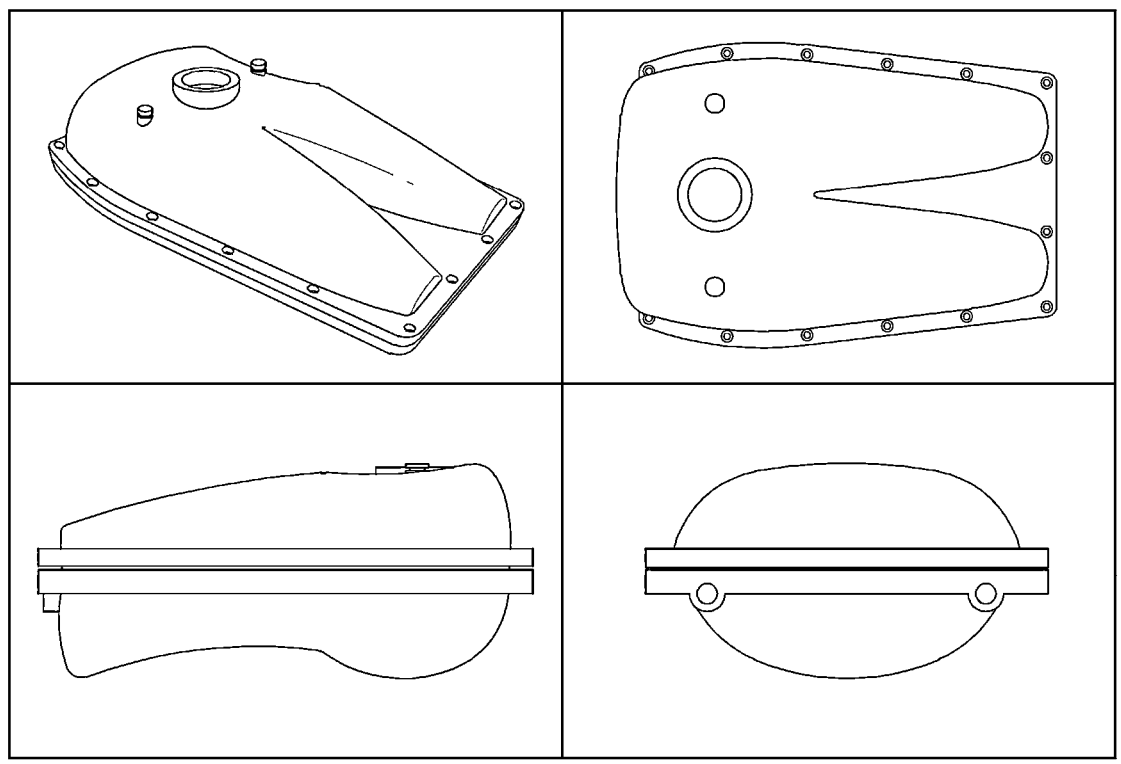
FIG. 2 illustrates phantom morphology mimicking the shape of the human lower body from waist to knee.

FIG. 1 shows positions of a phantom P and an array of four optical E-field sensors (OEFSs) 200 and two fiber-optic Bragg grating (FBG) temperature sensors 300 which are arranged on a surface of an artificial hip joint 100 in the phantom P. FIG. 2 illustrates the phantom morphology according to the present embodiment. Referring to FIGS. 1 and 2, the phantom P is a phantom for a human lower body, and was constructed based on data of Korean adult anthropometric standards for 6,413 Korean subjects (3,192 males and 3,221 females, aged 16 to 69 years).

As described in American Society for Testing and Materials (ASTM International) standard method for measurement of SARs, in order to simulate human tissue, a sealed plastic phantom container (with 15 mm thickness) was filled with about 20.8 L of a hydroxyethyl cellulose (HEC) gelled saline solution containing 24.2 g of NaCl, 483.6 g of HEC powder, and 20.8 L of distilled water.

Gel thermal characteristics (e.g., heat diffusivity=$1.4 \times 10^{-7}$ m$^2$/s and heat capacity=4,156 J/(kg·° C.)) were measured using a thermal characteristic analyzer (KD2, Decagon Devices Inc., Pullman, WA, USA). Electrical conductivity ($\sigma$=0.48±0.04 S/m at 64 MHz and 0.49±0.04 S/m at 128 MHz) and relative electrical permittivity ($\varepsilon r$=76.48±3.98 at 64 MHz and 76.22±4.12 at 128 MHz) of gels were measured using an evaluation kit (DAK-12, SPEAG Ltd., Zurich, Switzerland). Density ($\rho$=1.0095±0.0008 g/cm$^3$, at 22.4° C.) was measured using a pycnometer (SHEEN 1501/50, TQC Sheen Ltd., UK).

Artificial Hip Joint

Figures 3A, 3B:
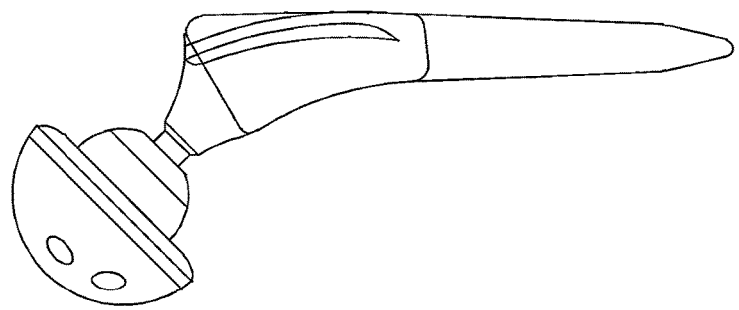
FIG. 3A is an assembly photograph of a hip joint implant used in an experiment according to an embodiment.
FIG. 3B illustrates computational modeling of each component of the hip joint implant according to the embodiment.

FIG. 3A is an assembly photograph of a hip joint implant 100 used in an experiment according to an embodiment, and FIG. 3B illustrates computational modeling of each component of the hip joint implant 100 according to the embodiment. Referring to FIGS. 3A and 3B, the hip joint implant 100 includes an acetabular cup 110 (B. Braun Medical Inc., PlasmacupSC, model No. NH050T), a cup liner 120 (Exactech Inc., Biolox delta, ceramic insert, model No. NH050T), a femoral head 130 (Exactech Inc., Biolox delta, ceramic femoral head, model No. NJ106D), and a femoral stem 140 (B. Braun Medical Inc., Excia 8/10 cementless, model No. NC413T). In FIG. 3A, the unit of length is centimeters. The artificial hip joint was immersed in the phantom P in a shape of a human lower body which was filled with an HEC gelled saline solution, as schematically illustrated in FIG. 1.

Numerical Simulation of SAR and RF Induction Heating at 3T

An SAR distribution of a phantom model was calculated using commercially available Sim4Life version 4.4 software (Zurich Med Tech, Zurich, Switzerland. https://zmt.swiss/sim4life/) and electromagnetics full wave solver (P-EM-FDTD), and a temperature distribution of the phantom model was calculated using a thermodynamic solver (P-THERMAL). A high-pass birdcage body coil was used as a body coil for homogeneous excitation. A high-pass birdcage body coil (a diameter of 62 cm and a length of 65 cm) was modeled using eight copper rungs attached to a copper shield (a diameter of 70 cm and a length of 120 cm) through 28 copper strips (2.5 cm×2.2 cm). Each rung consists of three individual copper strips, each having a length of 20 cm and a width of 2.5 cm, and includes four capacitor junctions. The dimensions of the coil and shield were based on the dimensions of a general body coil. The body coil was calibrated without a load. Four voltage sources were inserted in a gap of a rear end ring (top end of a head-first body model) at 45°, 135°, 225°, and 315° angular positions in terms of 4-port drive modeling. The voltage sources had the same voltage amplitude, and voltage phase values were 0°, 90°, 180°, and 270°. When the body coil was tuned in Sim4Life, IB1+I sensors were arranged in several positions, including the center of the coil, and the Gaussian pulses were applied to the voltage sources. By observing spectral peaks of the IB1+I sensors, capacitor values were adjusted until a desired homogeneous model frequency shifted to 127.88 MHz. Major concerns for a SAR numerical simulation were to check both the SAR distribution and high SAR position around the artificial hip joint was.

As illustrated in FIG. 3B, the modeling of the artificial hip joint was performed according to the sizes and materials of components of the hip joint. The phantom P was placed in the center of the coil rung and meshed with a finite differential time domain (FDTD) cell size of 3×3×3 mm$^3$. A uniaxial perfect match layer (UPML) was used for an absorption boundary condition. A rear surface of each model was located at a place spaced a distance of 18 cm apart from the farthest rung in a rearward direction. The characteristics of the human tissue were expressed using the Gabriel parameters of 128 MHz used in a dispersive fitting (DISPFIT) tool, and 1 and 5 were selected for the minimum and maximum numbers of variance poles, respectively. A numerical simulation of the FDTD was performed on an Intel Xeon Hexacore 2.3 GHz central processing unit (CPU) with Nvidia Tesla C2075 graphics processing unit (GPU).

Figure 4:
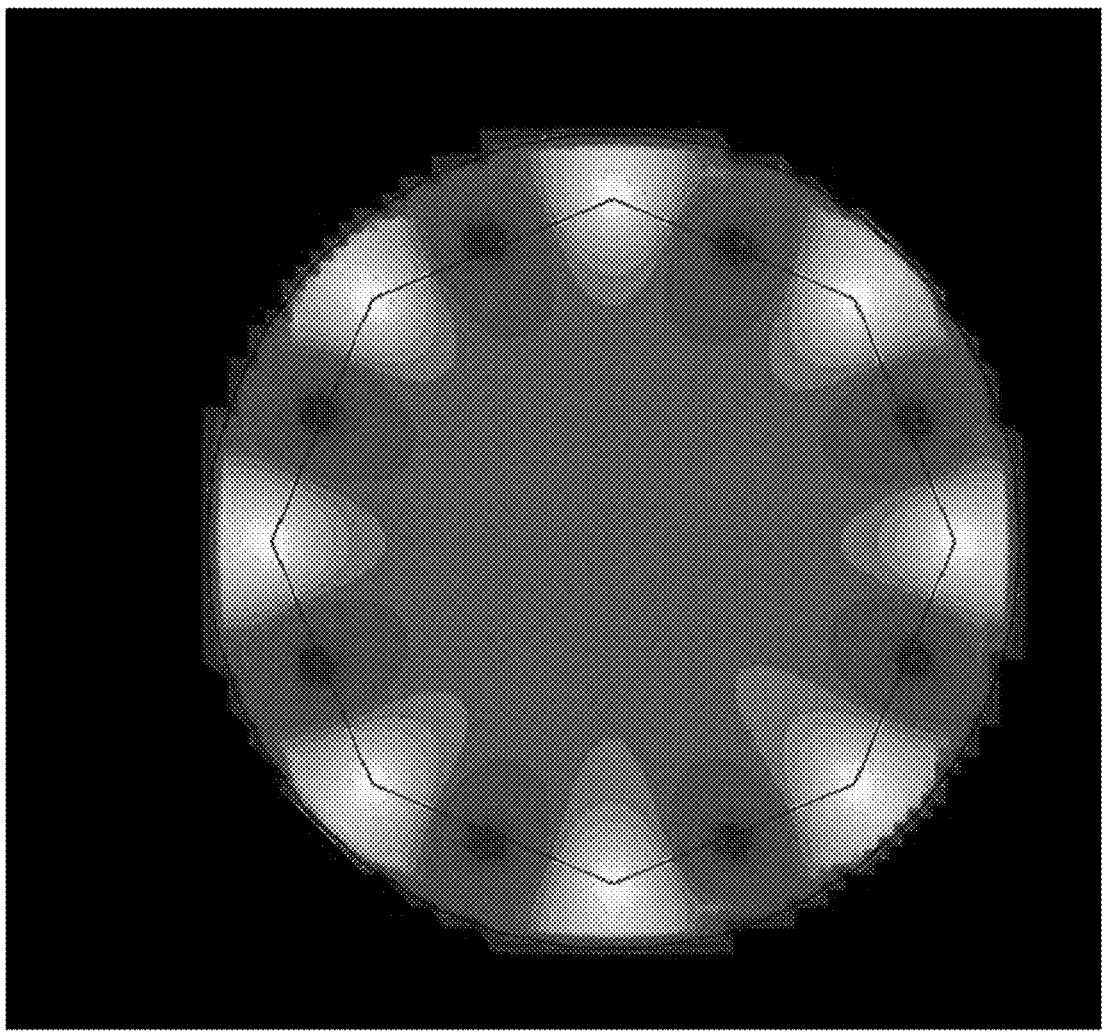
FIG. 4 shows the result of numerical analysis of a transverse slice of the RF magnetic field ($B1^+$) distributions obtained in the center of the unloaded body coil in the empty condition after coil tuning process.

FIG. 4 shows computer-simulated results of an RF magnetic field distribution formed inside a birdcage-shaped RF body coil. FIG. 4 illustrates a cross-sectional slice of the RF magnetic field distribution obtained from the center of the unloaded birdcage body coil in an empty state after the coil tuning process, and it can be seen that the RF magnetic field is uniform from the birdcage-shaped body coil toward the center.

The SAR distribution of the phantom irradiated with RF power was calculated using Equation 1 below.

$$SAR(\vec{r}, t, f) = \frac{\sigma(f) \times |\vec{E}(\vec{r}, t, f)|^2}{2\rho} \quad \text{[Equation 1]}$$

Here, $\sigma$ denotes electrical conductivity of the tissue, $\rho$ denotes the bulk density, $\vec{E}$ denotes a three-component E-field strength vector (x, y, z), $\vec{r}$ denotes a three-component spatial position vector (x, y, z), f denotes an RF, and t denotes an elapsed time. First, strength of an E-field was directly measured in three orthogonal directions using an E-field probe, and then amplitude of the E-field vector was obtained. The SAR value was obtained using Equation 1 without following the ASTM standard test methods. A normal-state solution of $\vec{E}$ when supplied with continuous wave RF power was directly used to calculate the SAR. Each SAR electromagnetic simulation using a continuous wave source was set at the International Electrotechnical Commission (IEC) 6 minutes whole body SAR limit of 2.0 W/kg in normal mode.

The ASTM F2181 standard test method was referred to check magnetic resonance (MR) heating for passive implants. The SAR and temperature rise were characterized by applying an RF magnetic field that produced a whole-body average SAR of 2 W/kg over the volume of the phantom. The SAR values were normalized to the whole-body average SAR of 2 W/kg.

The temperature of the phantom was modeled as a finite difference implementation of Pennes' bioheat transfer equation. For simplicity, a perfusion rate was assumed to be independent of time and temperature at a constant temperature of 37° C. and an ambient temperature of 25° C. in the phantom.

Independent SAR Measurement Using OEFS

Figure 5:
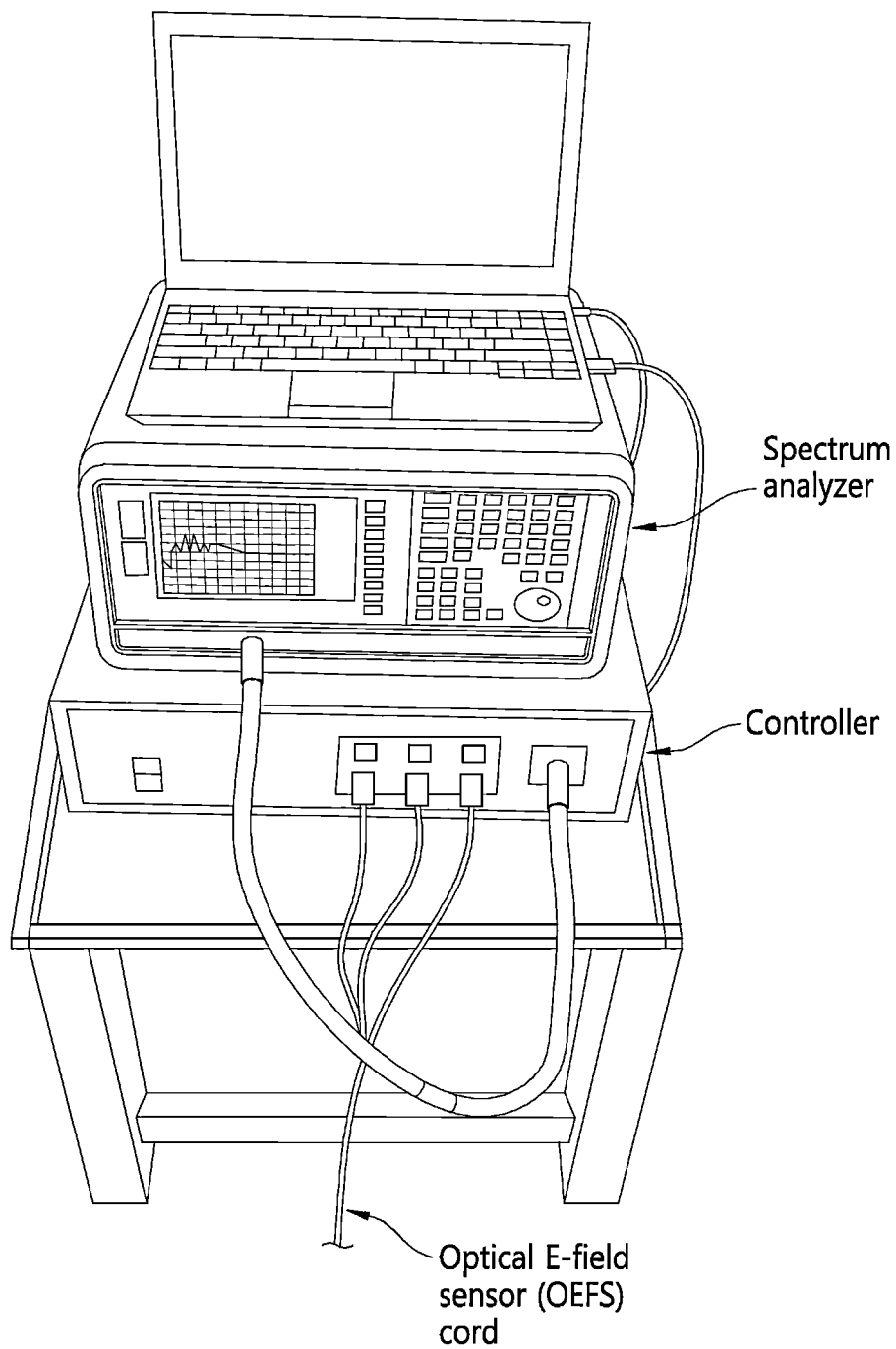
FIG. 5 is an overview of the experimental setup for independent measurement of electric field strength inside the phantom during MRI scanning.

FIG. 5 is a view illustrating an overall E-field measurement experimental setup. The four OEFSs illustrated in FIG. 1 were connected to a controller through a connection line which was connected to an end of each sensor. The controller was connected to a spectrum analyzer and a notebook computer to measure strength of an E-field.

The four OEFSs (model: SH-10EL, SEIKOH GIKEN Inc., Norcross, USA) 200 were disposed near a femoral head H and tail T of the femoral stem 140 showing a maximum SAR based on the simulation results (see FIG. 3B). The OEFSs 200 were used to measure the strength of the E-field in three-axis directions in each MRI scanner during repeated scans. The OEFSs 200 were calibrated for traceability using a transverse electromagnetic (TEM) cell. The SAR was determined using Equation 1 above. The OEFSs 200 were connected to a controller (model: C3-0355, SEIKOH GIKEN Inc., Norcross, USA) which was connected to a spectrum analyzer (model: 8560E, Agilent Technologies Inc., Santa Clara, CA, USA). The spectrum analyzer was connected to a personal computer using a universal interface bus (i.e., General Purpose Interface Bus (GPIB)) to read and record the strength of a three-dimensional E-field around an artificial hip joint. For measurement conditions of the controller and spectrum analyzer, central frequencies were set to 64 MHz at 1.5T and 128 MHz at 3T with span=±0.5 MHz respectively, a sweep was set to continuous, the reference and the display scales (LOG) of a reference level and amplitude were set to −10 dBm and 10 dB, a resolution bandwidth (RBW) was set to 0.005 MHz, a video bandwidth (VBW) was set to 0.001 MHz, a timeout response was set to one second, and a channel change interval was set to 100 ms in the case of automatic measurement with sampling number=200.

Temperature Measurement

Four fiber-optic temperature sensors (Neoptix Inc., Quebec, Canada) were disposed in the periphery of the phantom P. Heat loss to the environment was minimized during measurements for the artificial hip joint filled with gelled saline. An initial temperature of the sensor located inside the phantom P and a time it takes to reach equilibrium with the environment were measured. When a temperature difference between a temperature measured by the temperature sensor of the phantom and a temperature of an inside of a magnet hole was less than 0.05° C., it was considered that the phantom reached thermal equilibrium.

Figure 6:
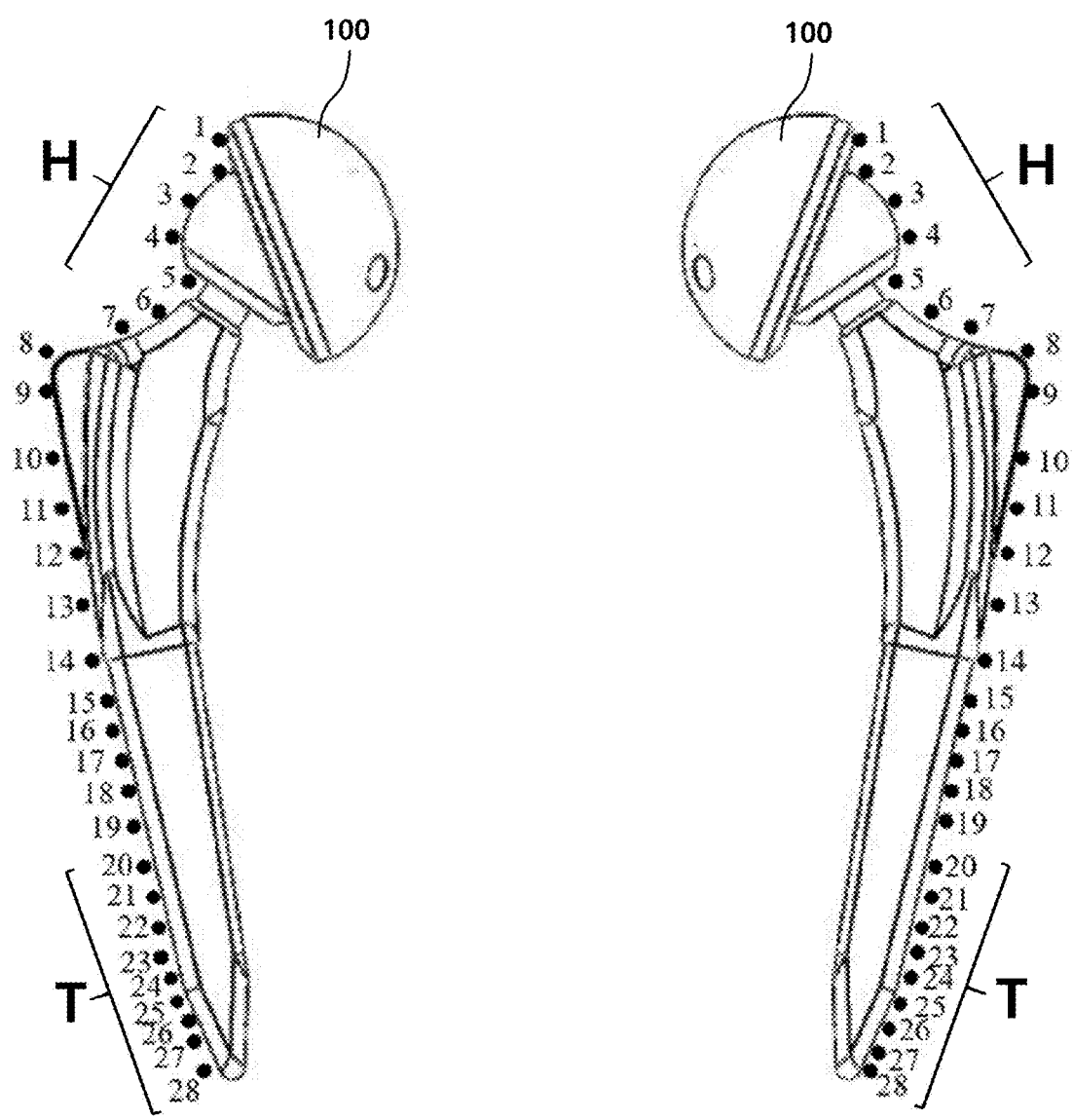
FIG. 6 illustrates a schematic diagram in which 28 fiber-optic Bragg grating temperature sensors per joint are disposed on a hip joint implant.

FIG. 6 is a view illustrating a state in which 28 FBG temperature sensors 300 per joint are disposed on a hip joint implant 100. Referring to FIG. 6, 56 FBG temperature sensors (SJ Photonics Co., South Korea, in a wavelength range 1510 to 1590 nm) 300 were located at two artificial hip joints to measure a change in temperature of artificial hip joints due to RF induction heating (see FIG. 1). The FBG temperature sensors 300 were connected to an interrogator (model: SJP-M-02-950, SJ Photonics Co. Ltd., South Korea) and connected to a personal computer to read and record a wavelength at a frequency of 970 Hz around the hip joints during MRI scans. Finally, the measured wavelength was converted into a temperature.

The FBG temperature sensors 300 (diameter 0.3 mm) minimizes the perturbations of an RF field. A temperature resolution of the FBG temperature sensor 300 system was 0.01° C. The FBG temperature sensor 300 was calibrated for traceability. The temperatures before and after the MRI scan were recorded according to a change in temperature in each MRI scanner, and a difference between the measured temperatures was calculated.

FIG. 7 shows measured temperature values according to an imaging time for each of five pieces of MRI equipment (Philips 1.5T MRI scanner, GE 1.5T MRI scanner, Siemens 3T MRI scanner, and two identical model Philips 3T MRI scanners) and for each MRI sequence used to acquire MRI images in each MRI equipment, using temperature sensors. A position for measuring a temperature was a temperature sensor #25 in a left hip joint of FIG. 6. As a result of measuring the temperatures, it can be shown that temporal temperature increases gradually with continuous RF irradiation during MRI scans.

Reference Local SAR without Hip Joint Implant and SAR with Implant

Similar to the ASTM standard test method, a change in local temperature was first measured at the same temperature sensor position as described above for temperature measurement, without a hip joint implant. The implant was then placed in the same position as measured above and the change in temperature was measured. The change in temperature measured in the above way was used to determine local SARs without implants and determine SARs with implants at each of the positions of the 56 temperature sensors 300 of a gelling saline phantom.

The SAR values may be obtained from the temperatures detected by the temperature sensors, and the SAR values are obtained as shown in Equation 2 below.

$$SAR = c_p \frac{\Delta \text{Temperature}}{\Delta \text{time}} \quad \text{[Equation 2]}$$

Here, $c_p$=4,156 J/(kg·° C.) denotes heat capacity of a gel material, ΔTemperature denotes a change in temperature [° C.] (i.e., a difference between a temperature measured when an artificial hip joint is inserted and a temperature measured before the artificial hip joint is inserted), and Δtime denotes a time [second] (i.e., scan time for each sequence).

All the measurements were repeated three times. The SARs obtained by the temperature measurements using the FBG temperature sensors 300 were compared with the SARs obtained by the E-field measurement using the OEFSs.

Arrangement of Artificial Hip Joint, Hip Joint Holder, OEFS Probe, and FBG Sensors Artificial hip joints 100, hip joint holders, OEFS probes 200, and FBG sensors 300 were disposed and immersed inside a phantom P filled with an HEC gelled saline solution so that a local E-field and a thermal environment were not disturbed according to ASTM guidelines. A vacuum was generated in a phantom container in order to remove air bubbles inside the gel mixture. The entire experimental setup was placed in a magnet hole of an MRI scanner for at least 24 hours to establish thermal equilibrium with the environment prior to MRI scanning.

Numerical Simulation of SAR and RF Induction Heating

Figure 8A:
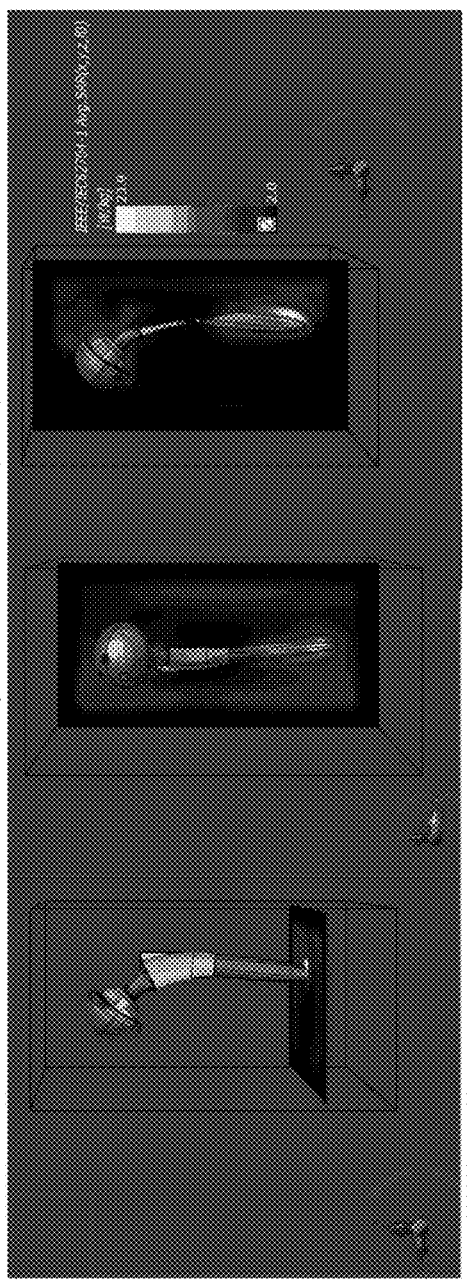
FIG. 8A shows computer-simulated SAR distributions.
Figure 8B:
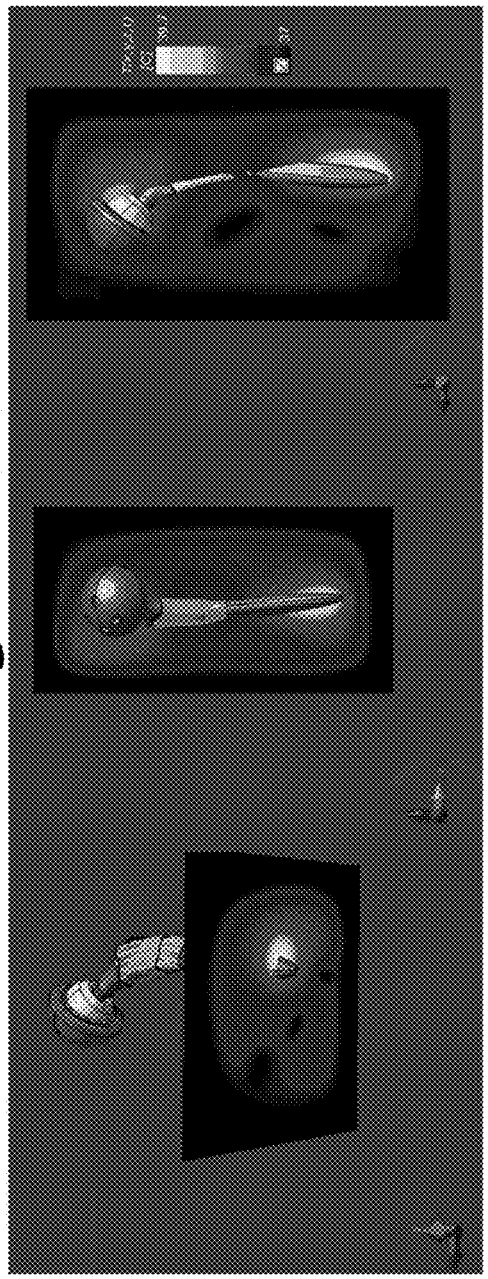
FIG. 8B illustrates computer-simulated temperature rise in a periphery of an artificial hip joint.

FIG. 8 shows computer-simulated SAR distributions and temperature rise at a periphery of artificial hip joints 100. Both high SAR and high temperature appeared near head and tail portions of the artificial hip joint 100. In particular, the SAR value was 23.9 W/kg with a background SAR (=2.0 W/kg) in the tail portion of the artificial hip joint. The local SAR values are normalized to the whole-body averaged SAR of 2 W/kg.

Study of Experimental Results

Reference Local SAR and Local SAR Levels in the Present of Hip Joint Implants

Figure 9A:
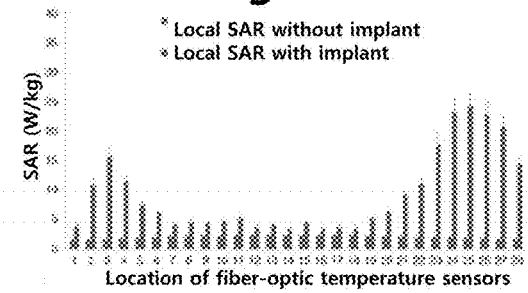
FIGS. 9A to 9J show local SAR levels with and without the artificial hip implants on the left and right sides of the hip joints at five different MRI scanners.
Figure 9B:
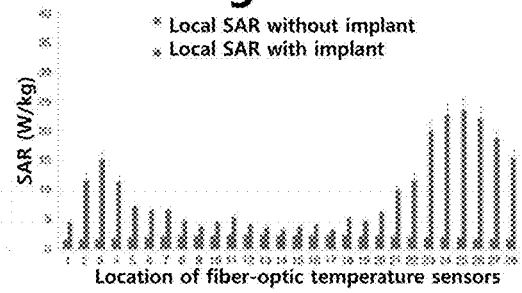
Figure 9C:
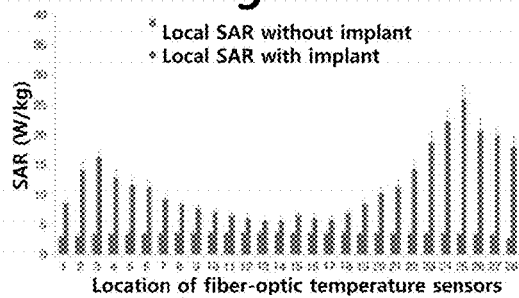
Figure 9D:
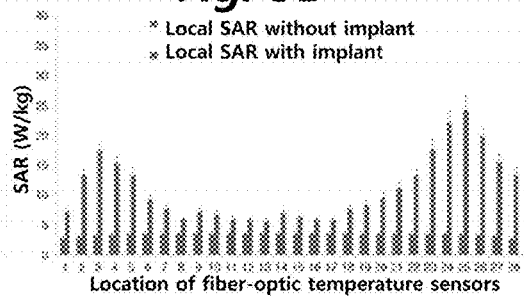
Figure 9E:
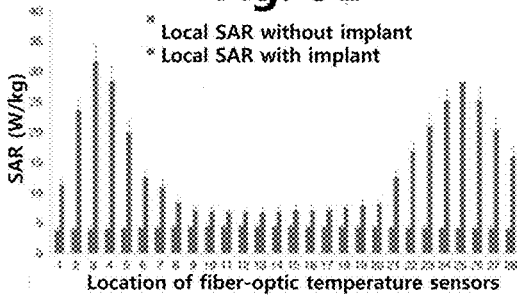
Figure 9F:
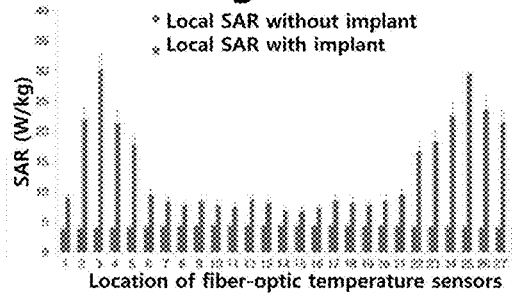
Figure 9G:
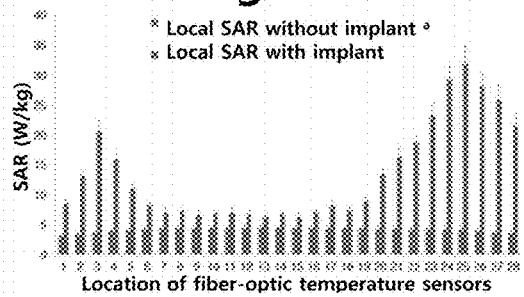
Figure 9H:
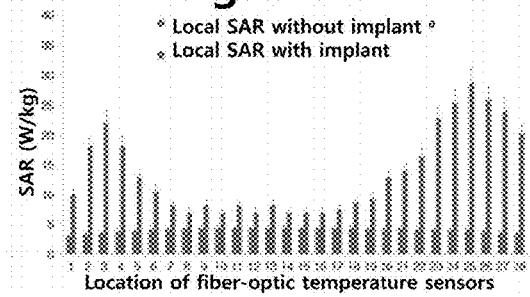
Figure 9I:
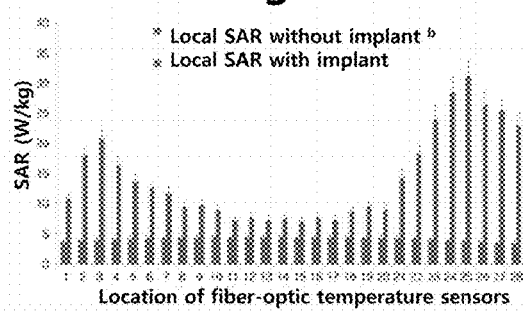
Figure 9J:
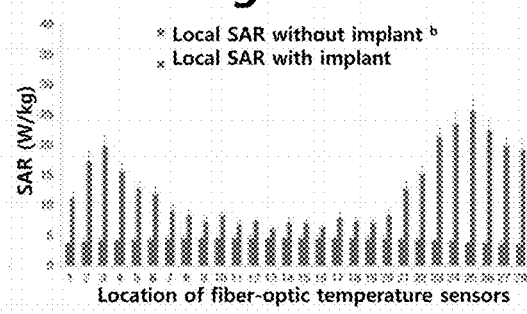
Figure 10A:
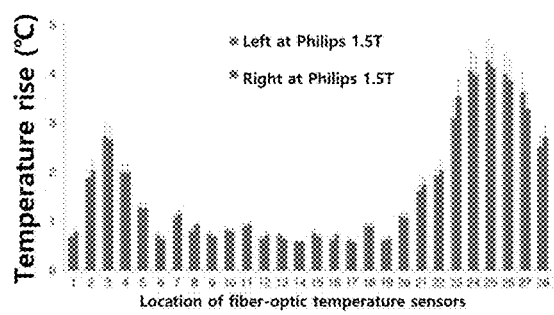
FIGS. 10A to 10E show experimentally measured temperatures via fiber-optic Bragg grating (FBG) sensors on both sides of the hip joints at five different MRI scanners by using a T1w TSE, IR TSE, or T1 TIRM sequence and imaging parameters.
Figure 10B:
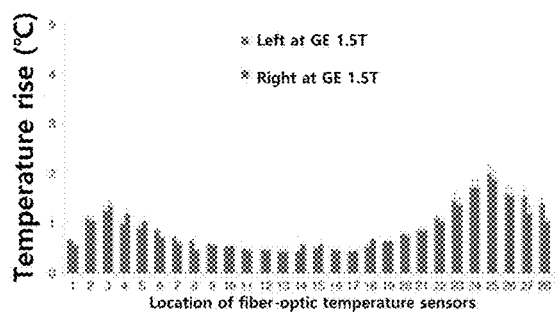
Figure 10C:
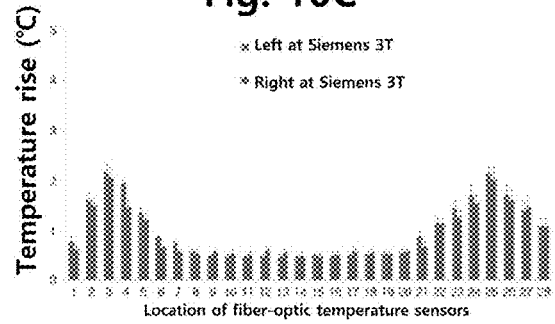
Figure 10D:
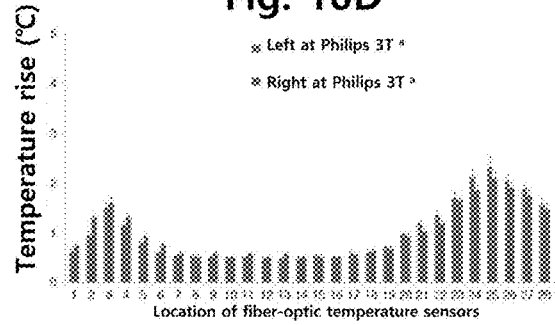
Figure 10E:
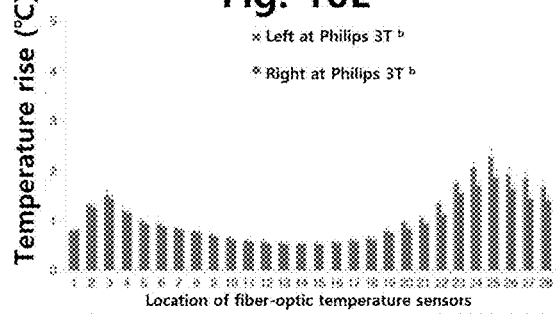

The reference local SAR represents an SAR level in the absence of implants. FIGS. 9A and 9B show local SAR levels with and without the implant in a T1w TSE sequence of a Philips 1.5T MRI system, wherein FIG. 9A shows a measurement result of a left hip joint implant and FIG. 9B shows a measurement result of a right hip joint implant. FIGS. 9C and 9D illustrate local SAR levels with and without the implant in an IR TSE sequence of a GE 1.5T system, wherein FIG. 9C shows a measurement result of a left hip joint implant and FIG. 9D shows a measurement result of a right hip joint implant. FIGS. 9E and 9F show local SAR levels with and without the implant in a T1 TIRM sequence of a Siemens 3T system, wherein FIG. 9E shows a measurement result of a left hip joint implant and FIG. 9F shows a measurement result of a right hip joint implant. FIGS. 9G, 9H, 9I, and 9J illustrate local SAR levels with and without the implant in a T1w TSE sequence of two same model Philips 3T system, wherein FIGS. 9G and 9I show measurement results of a left hip joint implant and FIGS. 9H and 9J show measurement results of a right hip joint implant.

In FIGS. 9A to 9J, horizontal axes indicate the positions of the FBG temperature sensors 300 (see FIG. 6), and vertical axes indicate the SAR levels (W/kg). In addition, the results (red color) indicate the SAR levels in the present of implants, and the results (blue color) indicate the SAR levels (reference local SAR level) in the absence of implants. Referring to FIGS. 9A to 9J, it can be seen that the SAR level is high in a head portion H (approximately positions #1 to #6) and a tail portion T (approximately positions #20 to #28) of the hip joint similarly in both of the left and right hip joint implants 100.

tABLE 1

| | Philips 1.5 T | | |
|---|---|---|---|
| Image sequence | T1w TSE | T1w SPIR | T2w TSE |
| Averaged local SAR with (without) implant (W/kg) | 9.37 (2.08) | 6.72 (2.08) | 4.91 (2.08) |
| SAR at OEFS #1 | 15.19 ± 1.22 | 7.96 ± 0.64 | 6.15 ± 0.46 |
| SAR at OEFS #2 | 23.82 ± 2.14 | 12.84 ± 1.16 | 9.41 ± 0.78 |
| SAR at OEFS #3 | 24.6 ± 2.16 | 11.46 ± 1.03 | 8.98 ± 0.76 |
| SAR at OEFS #4 | 16.82 ± 1.35 | 8.93 ± 0.68 | 5.67 ± 0.36 |

| | GE 1.5 T | | |
|---|---|---|---|
| Image sequence | T1w TSE | IR TSE | T2w TSE |
| Averaged local SAR with (without) implant (W/kg) | 11.83 (3.42) | 11.31 (3.42) | 11.56 (3.42) |
| SAR at OEFS #1 | 10.56 ± 0.84 | 16.92 ± 1.35 | 10.88 ± 0.87 |
| SAR at OEFS #2 | 8.61 ± 0.75 | 22.13 ± 1.77 | 9.21 ± 0.79 |
| SAR at OEFS #3 | 18.44 ± 1.66 | 24.3 ± 2.12 | 18.83 ± 1.68 |
| SAR at OEFS #4 | 14.83 ± 1.18 | 12.73 ± 1.14 | 15.77 ± 1.26 |

TABLE 2

| | Siemens 3T | | |
|---|---|---|---|
| Image sequence | T1w TSE | T1 TIRM | T2w TSE |
| Averaged local SAR with (without) implant (W/kg) | 12.09 (4.19) | 13.92 (4.19) | 11.73 (4.19) |
| SAR at OEFS #1 | 18.32 ± 1.47 | 19.14 ± 1.35 | 16.77 ± 1.34 |
| SAR at OEFS #2 | 19.86 ± 1.79 | 19.64 ± 1.47 | 20.57 ± 1.85 |
| SAR at OEFS #3 | 21.51 ± 1.84 | 22.74 ± 2.01 | 23.46 ± 2.11 |
| SAR at OEFS #4 | 27.68 ± 2.16 | 28.4 ± 2.17 | 25.42 ± 2.03 |

| | Philips 3T | | |
|---|---|---|---|
| Image sequence | T1w TSE | T1w SPIR | T2w TSE |
| Averaged local SAR with (without) implant (W/kg) | 13.61 (4.07) | 12.41 (4.07) | 11.93 (4.07) |
| SAR at OEFS #1 | 19.02 ± 1.45 | 18.51 ± 1.38 | 23.35 ± 1.78 |
| SAR at OEFS #2 | 25.03 ± 2.15 | 18.39 ± 1.56 | 14.68 ± 1.23 |
| SAR at OEFS #3 | 28.8 ± 2.39 | 13.53 ± 1.12 | 18.93 ± 1.61 |
| SAR at OEFS #4 | 17.43 ± 1.29 | 13.18 ± 1.05 | 15.57 ± 1.15 |

| | Philips 3 Tb | | |
|---|---|---|---|
| Image sequence | T1w TSE | T1w SPIR | T2w TSE |
| Averaged local SAR with (without) implant (W/kg) | 13.45 (4.24) | 11.94 (4.24) | 11.89 (4.24) |
| SAR at OEFS #1 | 18.16 ± 1.45 | 19.37 ± 1.45 | 16.38 ± 1.21 |
| SAR at OEFS #2 | 22.3 ± 1.98 | 16.68 ± 1.41 | 12.65 ± 1.04 |
| SAR at OEFS #3 | 27.6 ± 2.28 | 13.74 ± 1.14 | 20.3 ± 1.73 |
| SAR at OEFS #4 | 19.32 ± 1.45 | 14.35 ± 1.02 | 13.82 ± 0.99 |

Tables 1 and 2 show SAR values (mean±s.d.) measured by four OEFSs which are located at the head portion H and tail portion T of the artificial hip joint that are maximally heated in each scanner, according to numerical simulation results. Tables 1 and 2 also show an average of local SARs measured in the present of artificial hip joint implants and an average of local SARs measured in the absence of artificial hip joint implants from the head to the tail of the implant (a, b=two same model Philips 3T MRI systems).

A maximum SAR value measured by the Philips 1.5T MRI system was 24.6 W/kg at an OEFS #3 (near the tail portion of the hip joint) for the T1w TSE sequence. The maximum SAR value measured by the GE 1.5T system was 24.3 W/kg at OEFS #3 (near the tail) for the IR TSE sequence. A maximum SAR value measured by the Siemens 3T system was 28.4 W/kg at an OEFS #4 (near the head portion of the hip joint) for the T1 TIRM sequence. Maximum SAR values measured by the Philips 3T systems, which are two identical models, were 28.8 and 27.6 W/kg at an OEFS #3 (near the tail portion) for the T1w TSE sequence.

Comparison of SAR Levels Obtained by E-Field Measurement with Those Obtained by Temperature Measurement in Hottest Portions A difference between E-field-based SAR quantification and temperature-based SAR quantification was 8.8% or less in the Philips 1.5T MRI system, was 7.4% or less in the GE 1.5T system, was 8.3% or less in the Siemens 3T system, and was 9.1% or less and 9.4% or less in the two same model Philips 3T MRI models, respectively.

Measured Temperature Rise at 1.5T and 3T MRI Scanners

As a result of showing that heat loss to the environment is minimized during measurements, an initial temperature of the phantom measured by the temperature sensor ranged from 27.8 to 28.3° C., compared to temperature inside a magnet bore ranging from 23.6 to 25.4° C., and it took a minimum of 3 hours and 52 minutes to reach thermal equilibrium with the environment in the five MRI systems.

FIG. 10 shows a temperature rise measured with FBG temperature sensors located near a pair of artificial hip joints for each scanner by using a T1w TSE, IR TSE, or T1 TIRM sequence and imaging parameters. A peak temperature rise measured in the T1w TSE sequence (scan time=12 minutes and 12 seconds) of the Philips 1.5T system was 4.22° C. (FIG. 10A) and a peak temperature rise measured in the IR TSE sequence (scan time=5 minutes and 20 seconds) of the GE 1.5T system was 1.99° C. (FIG. 10B), wherein the peak temperature rises occurred near the tail portion of the hip joint. A peak temperature rise measured in the T1 TIRM sequence (scan time=4 minutes and 44 seconds) of the Siemens 3T system was 2.16° C. and occurred near the head portion of the hip joint (FIG. 10C). A peak temperature rises measured in the T1W TSE sequence (scan time=5 minutes and 6 seconds) of the two identical Philips 3T models were 2.33 and 2.24° C. and occurred in the tail portion of the hip joint (FIGS. 10D and 10E).

Results and Review

As the preference for MRI increases, it is likely that more patients with implanted metal devices will receive MRI scans. In this regard, RF induction heating caused by hip joint implants, cardiovascular implants, knee arthroplasty, neurosurgical implants, implantable microstiumulators, orthopedic plate implants, straight stainless steel rods, and stents may pose an issue with MRI safety of patients.

RF dosimetry using an E-field probe will be an important tool for MRI safety. The above method does not require long scan times to observe SAR levels. The OEFS sensors were calibrated for traceability and the results were read easily. The E-field is not uniform even in a generally uniform B1 field. The sensors used in this invention are small in size and effectively measure a power level of a point in space. The sensors simultaneously measure the E-fields as a vector in all three directions in space.

In the present embodiment, the maximum SAR value experimentally measured with the phantom by the MRI system in a maximum RF irradiation environment was about 28.8 W/kg at 3T. The numerical simulation indicate that a highly non-uniform E-field was generated in adjacent portions of the head and tail portions of the artificial hip joint, resulting in high SAR and RF induction heating, and the results of the numerical simulation are consistent with the experimental measurements.

When there is no hip joint implants, the local SAR level in the body part of the implant was slightly higher than the SAR levels in the head and tail portions. However, when the hip joint implant is placed, the local SAR levels in the head and tail portions were much higher than the local SAR value in the body part of the implant. The local SAR levels with implants were at least 5 times higher in the head portion of the artificial hip joint and 7 times higher in the tail portion than the local SAR levels without implants at the same measurement positions.

According to IEC 60601-2-33 standard, a maximum SAR for the whole body is limited to 2.0 W/kg, a maximum temperature is limited to 39° C., and a core temperature rise is limited to 0.5° C. In the present embodiment, the temperature rise measured by the FBG temperature sensors indicates that RF induction heating appears in the head and tail portions of the artificial hip joint. In addition, the maximum temperature rise (=4.22° C.) measured at 1.5T occurred in the tail portion of the hip joint, and the measured high temperature rise (=2.84° C.) was also found in the head portion of the implant. Similar results were also found at 3T. A half wavelength of an RF field in human tissue is about 13 cm at 3T and is 25 cm at 1.5T. A half wavelength conductor resonates with an RF and leads a high level of heating. In the present embodiment, a total length of the hip joint is about 20 cm (not applicable when a cup and a tail are insulated from each other) in the middle of a half wavelength of 1.5T and 3T. In consideration of these facts, it is expected that the artificial hip joint will not cause a very high temperature rise, which is consistent with the results of the present embodiment. As can be seen from the temperature measured at the tip of the implant as a function of scan times, the measured temperature was non-linearly increased due to heat transfer to the surrounding gelled salt phantom and also due to a change in eddy current of the tip of the implant with a large curvature.

In the present embodiment, the single scan time ranges from 3 to 12 minutes. In the ASTM F2182-09 standard test method, since a reasonable maximum time is considered as a single clinical scan and a temperature tends to increase almost proportionally with an RF irradiation time, 15 minutes of continuous RF irradiation is required. In fact, most clinical MRI scans require a total scan time of up to 1 hour, according to the body portion being imaged, clinical signs, and patient tolerance. Although each individual sequence typically does not exceed 15 minutes, a pause time between the sequences may be very short and accumulated heating may exceed 15 minutes of continuous scans.

As compared to the related art, the use of the OEFSs allows for direct and reliable RF E-field and SAR level measurements and also allows comparison of SAR levels at multiple positions inside a gelled-saline phantom. A large variability of SAR was observed. The high SAR levels measured by the OEFSs were found in the head and tail portions of the artificial hip joints. The measured local SAR values were similar to the numerical simulation results and exceeded the acceptable limits. In the present embodiment, the positions representing the temperature rise of a titanium alloy implant in the numerical calculation are consistent with those representing the temperature rise of the titanium alloy implant in the experimental measurements using three different MRI sequences at different magnetic field strengths of 1.5T and 3T. High temperature rise was observed in the head portion as well as the tail portion of the hip joint implant. Another important feature of the present embodiment is a calorimetry method using 28 temperature sensors (56 temperature sensors in total) on each artificial hip joint compared to four sensors commonly used in the ASTM F2182-09 standard. A plurality of sensors were used, and thus accurate, reliable, and realistic evaluation of temperature distributions may be obtained without missing the SAR value obtained from the hottest portions, and the SAR values obtained from the E-field measurements and temperature measurements are consistent with each other.

Thus, the results and experimental methods which are obtained in the present embodiment may play an important role in evaluating safety of patients in acquiring medical images from patients with artificial hip joint implants in MRI. Furthermore, the methods according to the present embodiment are applied to different artificial hip joints, different MRI vendors, or other scan sequences to measure SARs and temperature rise and estimate RF heating and body tissue damage.

The above description of the present invention is only exemplary, and it will be understood by those skilled in the art that various modifications can be made without departing from the scope of the present invention and without changing essential features. Therefore, the above-described embodiments should be considered in a descriptive sense only and not for purposes of limitation.

What is claimed is:

1. A method of measuring a specific absorption rate (SAR) of a hip joint implant using magnetic resonance imaging (MRI), the method comprising:
   arranging the hip joint implant in a human lower body-shaped phantom;
   arranging an optical electric field sensor around the hip joint implant;
   providing radio frequency (RF) energy according to an MRI sequence to the human phantom; and
   calculating the SAR of the hip joint implant from strength of an electric field measured by the optical electric field sensor;
   wherein the calculating of the SAR of the hip joint implant includes calculating Equation $$SAR(\vec{r}, t, f) = \frac{\sigma(f) \times |\vec{E}(\vec{r}, t, f)|^2}{2\rho},$$

where, $\sigma$ denotes electrical conductivity of tissue, $\rho$ denotes the bulk density, $\vec{E}$ denotes a three-component electric field strength vector (x, y, z), $\vec{r}$ denotes a three-component spatial position vector (x, y, z), f denotes an RF, and t denotes an elapsed time.

2. The method of claim 1, wherein the hip joint implant is formed in a shape extending from a head portion to a tail portion,
   wherein the hip joint implant further includes a plurality of temperature sensors disposed on the hip joint implant from the head portion to the tail portion.

3. The method of claim 2, wherein the plurality of temperature sensors are fiber-optic Bragg grating temperature sensors.

4. A method of measuring temperature rise of a hip joint implant using magnetic resonance imaging (MRI), the method comprising:
   arranging the hip joint implant in a human lower body-shaped phantom;
   arranging a plurality of temperature sensors on the hip joint implant;
   providing radio frequency (RF) energy according to an MRI sequence to the human phantom;
   measuring, by the temperature sensors, a change in temperature of the hip joint implant;
   calculating, by the temperature sensors, a specific absorption rate (SAR) of the hip joint implant from the measured temperatures;
   wherein the plurality of temperature sensors are configured to:
      measure ambient temperatures of the hip joint implant; and
      calculate the SAR of the hip joint implant from the measured temperatures;
   wherein the SAR is obtained by calculating Equation $$SAR = c_p \frac{\Delta \text{Temperature}}{\Delta \text{time}}$$

here, $c_p$=4,156 J/(kg·° C.), $c_p$ denotes heat capacity of a gel material, ΔTemperature denotes a change in temperature in degree Celsius (° C.), the change in temperature ° C. is a difference between a temperature measured when an artificial hip joint is inserted and a temperature measured before the artificial hip joint is inserted, and Δtime denotes a time in seconds, the time in seconds is an image capturing time for each sequence.

5. The method of claim 4, wherein the hip joint implant is formed in a shape extending from a head portion to a tail portion,
   wherein the plurality of temperature sensors are disposed on the hip joint implant from the head portion to the tail portion.

6. The method of claim 5, wherein the plurality of temperature sensors are fiber-optic Bragg grating temperature sensors.

* * * * *